US012673016B2

(12) United States Patent
Chen et al.

(10) Patent No.: US 12,673,016 B2
(45) Date of Patent: Jul. 7, 2026

(54) COACERVATE CLEANSING COMPOSITION COMPRISING A BETAINE/GLYCOLIPID SURFACTANT SYSTEM

(71) Applicant: L'OREAL, Paris (FR)

(72) Inventors: Changlong Chen, Edison, NJ (US); Siliu Tan, Westfield, NJ (US); Mariko Hasebe, New York, NY (US)

(73) Assignee: L'OREAL, Paris (FR)

( * ) Notice: Subject to any disclaimer, the term of this patent is extended or adjusted under 35 U.S.C. 154(b) by 300 days.

(21) Appl. No.: 18/525,456

(22) Filed: Nov. 30, 2023

(65) Prior Publication Data

US 2025/0177273 A1 Jun. 5, 2025

(51) Int. Cl.

| | |
|---|---|
| ***C11D 1/92*** | (2006.01) |
| ***A61K 8/04*** | (2006.01) |
| ***A61K 8/44*** | (2006.01) |
| ***A61K 8/46*** | (2006.01) |
| ***A61K 8/60*** | (2006.01) |
| ***A61K 8/73*** | (2006.01) |
| ***A61K 8/84*** | (2006.01) |
| ***A61Q 19/10*** | (2006.01) |

(52) U.S. Cl.

CPC ................ *A61K 8/466* (2013.01); *A61K 8/04* (2013.01); *A61K 8/442* (2013.01); *A61K 8/608* (2013.01); *A61K 8/736* (2013.01); *A61K 8/84* (2013.01); *A61Q 19/10* (2013.01); *A61K 2800/30* (2013.01)

(58) Field of Classification Search

CPC .. C11D 1/90; C11D 1/92; C11D 7/268; C11D 9/225; C11D 9/262; C11D 3/0094; C11D 2111/12

See application file for complete search history.

(56) References Cited

U.S. PATENT DOCUMENTS

| | | | | |
|---|---|---|---|---|
| 2014/0349902 | A1* | 11/2014 | Allef | A61K 8/361 510/491 |
| 2021/0371773 | A1* | 12/2021 | Brandt | C12N 9/1048 |
| 2022/0118035 | A1* | 4/2022 | Buzzi | A61K 31/197 |
| 2022/0183958 | A1* | 6/2022 | Kleinen | A61K 8/90 |
| 2023/0107595 | A1* | 4/2023 | Zhu | A61K 8/65 424/70.13 |
| 2023/0414478 | A1* | 12/2023 | Cavaco Paulo | A61K 8/737 |
| 2024/0156706 | A1* | 5/2024 | Hutton, III | A61Q 5/02 |
| 2025/0154435 | A1* | 5/2025 | Haight | C11D 1/83 |

FOREIGN PATENT DOCUMENTS

| | | | |
|---|---|---|---|
| WO | 2023200753 | A1 | 10/2023 |
| WO | 2024097599 | A1 | 5/2024 |

OTHER PUBLICATIONS

Search Report issued to French counterpart Application No. FR2400596 dated Aug. 12, 2024.

Zarrintaj et al. "Polylysine for skin regeneration: A review of recent advances and future perspectives," Bioengineering & Translational Medicine, vol. 7, No. 1, Nov. 5, 2021.

Guzman et al. "Chitosan: A Promising Multifunctional Cosmetic Ingredient for Skin and Hair Care," Cosmetics, vol. 9, No. 5, Sep. 27, 2022.

Kakizawa et al. "Creation of New Functions by Combination of Surfactant and Polymer—Complex Coacervation with Oppositely Charged Polymer and Surfactant for Shampoo and Body Wash," Journal of Oleo Science, 2019, 68, 6, 525-539.

Anonymous, Mintel, "Beste No. 9 Jelly Cleanser," Record ID 9608550, May 2022, www.mintel.gnpd.

* cited by examiner

*Primary Examiner* — Charles I Boyer

(74) *Attorney, Agent, or Firm* — McNees Wallace & Nurick LLC

(57) ABSTRACT

The disclosure relates to compositions comprising (a) at least one amphoteric surfactant, (b) at least one glycolipid, (c) at least one cationic polymer from about 0.05% to about 2%; and (d) at least one cosmetically acceptable solvent wherein the cleansing system is essentially free of phenoxyethanol, and wherein the pH of the composition is between 4 and 8, and wherein the ratio of a to b is from about 0.4 to about 4, and wherein the total concentration of a and b combined is about 10 to about 20% of the total weight of the composition. The compositions can be used as rinse-off compositions for cleansing skin.

16 Claims, 1 Drawing Sheet
(1 of 1 Drawing Sheet(s) Filed in Color)

COACERVATE CLEANSING COMPOSITION COMPRISING A BETAINE/GLYCOLIPID SURFACTANT SYSTEM

TECHNICAL FIELD

The present disclosure is directed to a skin care composition, in particular, a coacervate cleansing composition.

BACKGROUND

Current skincare routines usually require multiple steps and multiple products to achieve desired skincare results. Typical skincare routines usually include a skin cleansing step followed by another product to impart various skin benefits such as hydration, anti-aging, or anti-acne. Common skin cleansing products usually rely on surfactants to provide cleansing and do not deposit skincare actives onto the skin.

There is a need in the market for skin cleansing compositions to provide enhanced deposition of skincare actives. As such, consumers desire new and improved skin cleansing compositions that can cleanse the skin and also provide skincare benefits more efficiently.

SUMMARY

In various embodiments, provided is a coacervate cleansing system, comprising:

(a) at least one amphoteric surfactant;

(b) at least one glycolipid;

(c) at least one cationic polymer from about 0.05% to about 2%; and (d) at least one cosmetically acceptable solvent wherein the cleansing system is essentially free of phenoxyethanol, and wherein the pH of the composition is between 4 and 8, and wherein the ratio of a to b is from about 0.4 to about 4, and wherein the total concentration of a and b combined is about 10 to about 20% of the total weight of the composition.

In some embodiments, provided is a coacervate cleansing system, comprising:

(a) at least one amphoteric surfactant selected from the group consisting of cocamidopropyl hydroxysultaine and coco betaine from about 3% to about 8% by weight, relative to the total weight of the composition;

(b) at least one glycolipid selected from the group consisting of rhamnolipid and sophorolipid from about 2% to about 7% by weight, relative to the total weight of the composition;

(c) at least one cationic polymer selected from the group consisting of chitosan and polylysine from about 0.1% to about 0.2%; and (d) water wherein the cleansing system is essentially free of phenoxyethanol, and wherein the pH of the composition is between 4 and 8, and wherein the ratio of a to b is about 0.4 to about 4.

In some embodiments, provided is a method for cleansing skin comprising applying to the skin of a subject a coacervate cleansing system, comprising:

(a) at least one amphoteric surfactant;

(b) at least one glycolipid;

(c) at least one cationic polymer from about 0.1% to about 1%; and (d) at least one cosmetically acceptable solvent wherein the cleansing system is essentially free of phenoxyethanol, and wherein the pH of the composition is between 4 and 8, and wherein the ratio of a to b is about 0.4 to about 4, and wherein the total concentration of a and b combined is about 10% to about 20% of the total weight of the composition.

The coacervate system described in this invention is a unique phenomenon that demonstrates enhanced stability which is beneficial when cleansing the skin. The coacervate phenomenon is demonstrated through the phase transition of the system by initially appearing clear, but then appearing cloudy upon dilution with water. This coacervate cleansing systems provides a unique cleansing experience marked by enhanced foaming properties and good stability. It has surprisingly been found that compositions with the above disclosed ratio of glycolipids to amphoteric surfactants demonstrate the coacervate phenomenon.

The glycolipids in this invention can be used for cleansing purposes, but also have antimicrobial properties. The coacervate cleansing system described has unique physical characteristics, and transitions into a foaming state when diluted with water which could enhance deposition of skincare benefits onto the skin.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
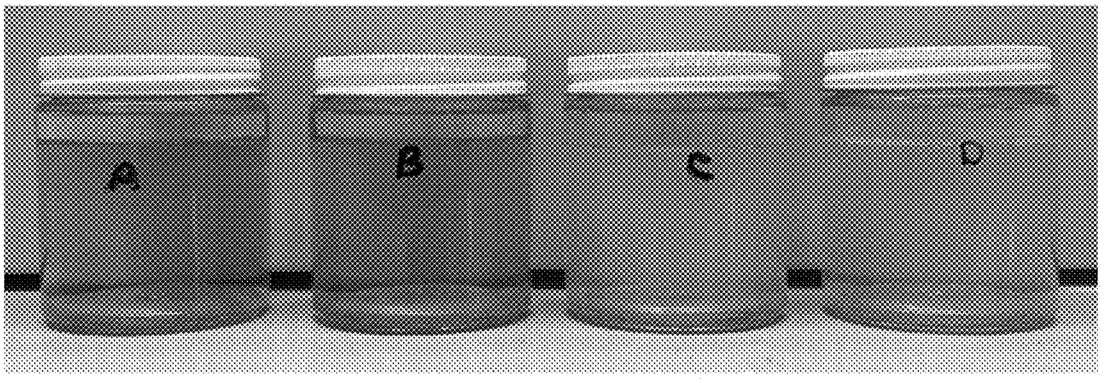
FIG. 1. Coacervate cleansing system compositions A-D before dilution.

It is to be understood that the foregoing and following descriptions are exemplary and explanatory only, and are not intended to be restrictive of any subject matter claimed.

DETAILED DESCRIPTION

The disclosure relates to compositions for cleansing skin and methods of using the compositions.

I. Compositions

Amphoteric Surfactants:

In the various embodiments, the cosmetic cleansing composition comprises at least one amphoteric surfactant (or zwitterionic surfactant). In some embodiments, the cosmetic cleansing composition may include or excludes any one or more of nonionic, cationic, or anionic surfactants. In some embodiments, the cosmetic cleansing composition includes a combination amphoteric surfactants.

In some embodiments, the at least one amphoteric surfactant may include alkyl betaine, alkylamidopropyl betaine, alkyl hydroxysultaine, alkylamidopropyl hydroxysultaine, lauryl hydroxysultaine, alkylamidopropylamine N-oxide, alkyldimethylamine N-oxide, cocamidopropyl hydroxysultaine, cocamidopropyl betaine, coco betaine, sodium lauroamphoacetate, disodium cocoamphodiacetate, or a combination thereof. In preferred embodiments, the amphoteric surfactant is selected from cocamidopropyl hydroxysultaine and coco betaine.

In some embodiments the at least one amphoteric surfactant may be selected from, for example, betaines, alkyl sultaines, alkyl amphoacetates and alkyl amphodiacetates, alkyl amphoproprionates, amphocarboxylates, alkyl betaines, amidoalkyl betaines, amphophosphates, phosphobetaines, pyrophosphobetaines, carboxyalkyl polyamines, amidoalkyl sultaines, salts thereof, or mixtures thereof.

Betaines which can be used in the current compositions include those having the formulas below:

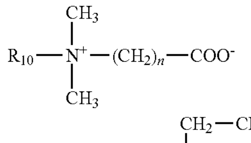

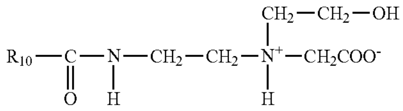

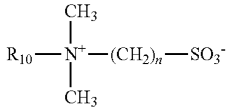

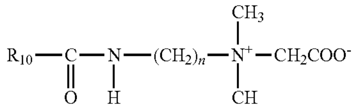

wherein $R^{10}$ is an alkyl group having 8-18 carbon atoms; and n is an integer from 1 to 3.

Particularly useful betaines include, for example, cocoamidopropyl hydroxysultaine, coco betaine, cocoamidopropyl betaine, lauryl betaine, laurylhydroxy sulfobetaine, lauryldimethyl betaine, behenyl betaine, capryl/capramidopropyl betaine, lauryl hydroxysultaine, stearyl betaine, and mixtures thereof.

Hydroxyl sultaines useful in the compositions of the invention include the following

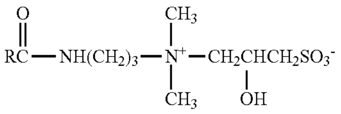

wherein

R is an alkyl group having 8-18 carbon atoms.

More specific examples include, but are not limited to cocamidopropyl hydroxysultaine, lauryl hydroxysultaine, or mixtures thereof.

Useful alkylamphoacetates include those having the formula

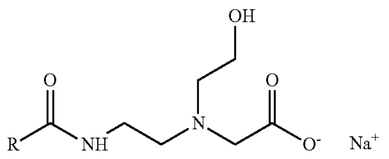

wherein

R is an alkyl group having 8-18 carbon atoms.

useful alkyl amphodiacetates include those having the formula

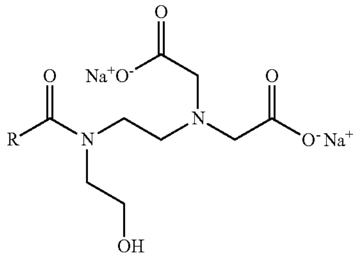

wherein

R is an alkyl group having 8-18 carbon atoms.

Exemplary and non-limiting examples of useful alkyl amphopropionates include cocoamphopropionate, caprylamphopropionate, cornamphopropionate, caproampho-propionate, oleoamphopropionate, isostearoamphopropionate, stearoamphopropionate, lauroamphopropionate, salts thereof, or mixtures thereof.

The at least one amphoteric surfactant of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

In preferred embodiments, the at least one amphoteric surfactant is chosen from cocamidopropyl hydroxysultaine, coco betaine, or mixtures thereof.

The total concentration of the at least one amphoteric surfactant and the at least one glycolipid is about 10% to about 20% of the total weight of the composition. The ratio of the at least one amphoteric surfactant to the at least one glycolipid is from about 0.4 to about 4. The at least one amphoteric surfactant may be present in the cosmetic cleansing composition, for example, in a range for example from about 3% to about 8%, based on the weight of the cosmetic cleansing composition.

For example, the at least one amphoteric surfactant can be present in the cosmetic cleansing composition according to the disclosure from about 3% to about 8%, or from about 3% to about 7%, or from about 3% to about 6%, or from about 3% to about 5%, or from about 3% to about 4%, or from about 3% to about 8%, or from about 4% to about 8%, or from about 5% to about 8%, or from about 6% to about 8%, or from about 7% to about 8%, or any suitable combination, sub-combination, range, or sub-range thereof by weight, based on the weight of the cosmetic cleansing composition. One of ordinary skill in the art, however, will appreciate that other ranges are within the scope of the invention.

Glycolipids:

The composition according to the invention comprises one or more glycolipids.

The term "glycolipid" is understood as meaning a compound formed from a lipid to which are attached one or more sugar compounds.

The one or more glycolipids may be selected from rhamnolipids, sophorolipids, glucolipids, trehalolipids, cellobiose lipids, mannosylerythritol lipid, and mixtures thereof.

Glucolipids:

The one or more glycolipids may be glucolipids, which contain a glucose moiety and can be represented by the general formula (I):

(I)

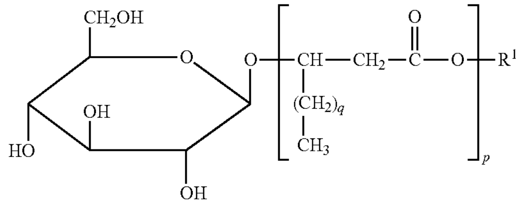

in which:

- R1 represents a hydrogen atom or a cation,
- p denotes an integer ranging from 1 to 4, and
- q denotes an integer ranging from 4 to 10, preferably equal to 6.

The glucolipids can be produced by the bacterium *Alcaligenes* sp. MM1.

The appropriate fermentation methods are reviewed by M. Schmidt in his doctoral thesis (1990), Technical University of Braunschweig, and by Schulz et al. (1991) Z. Naturforsch., 46C, 197-203. The glucolipids are recovered from the fermentation broth by solvent extraction using diethyl ether or a dichloromethane:methanol or chloroform:methanol mixture.

Sophorolipids:

The one or more glycolipids may be sophorolipids, which contain a sophorose moiety and can be represented by the general formula (II):

(II)

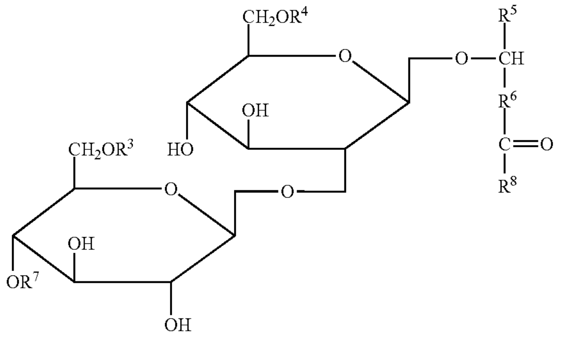

in which:

- R3 and R4 individually represent a hydrogen atom or an acetyl group,
- R5 represents a saturated or unsaturated, hydroxylated or non-hydroxylated hydrocarbon group having from 1 to 9 carbon atoms, preferably methyl,
- R6 represents a saturated or unsaturated, hydroxylated or non-hydroxylated hydrocarbon group having from 1 to 19 carbon atoms, with the proviso that the total number of carbon atoms in the groups R5 and R6 does not exceed 20 and is preferably from 14 to 18.

Sophorolipids may be incorporated into the composition according to the invention either in the form of the open-chain free acid, where R7 represents a hydrogen atom and R8 represents a hydroxy group OH, or in its lactone form, where a lactone ring is formed between R7 and R8, as indicated by formula (III):

(III)

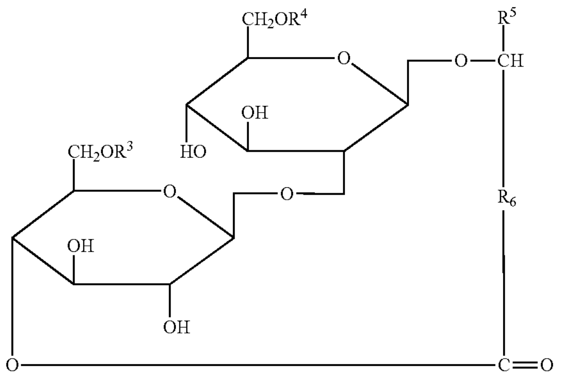

in which:

- R3, R4, R5 and R6 are as defined above, with the proviso that at least one of R3 and R4 represents an acetyl group.

The sophorolipids can be produced by yeast cells, for example *Torulopsis apicola* and *Torulopsis bombicola* cells. The fermentation process generally uses sugars and alkanes as substrates.

Appropriate fermentation methods are reviewed in A. P. Tulloch, J. F. T. Spencer and P. A. J. Gorin, Can. J. Chem. (1962), 40, 1326, and U. Gobbert, S. Lang and F. Wagner, Biotechnology Letters (1984), 6 (4), 225. The resulting product is a mixture of various open-chain sophorolipids and of sophorolipid lactones that may be used in the form of mixtures, or the required form may be isolated.

It is possible to use as sophorolipids for example that sold under the Sopholiance S name by Givaudan and that sold under the BioToLife name by BASF.

Trehalolipids

The one or more glycolipids may be trehalolipids, which contain a trehalose fragment and can be represented by the general formula (IV):

(IV)

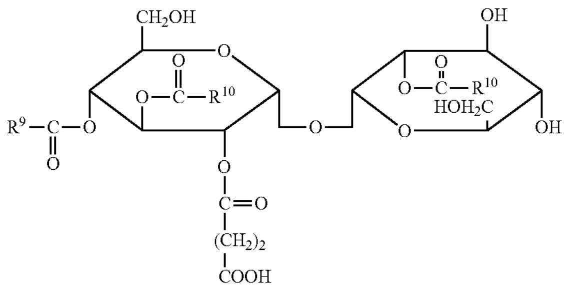

in which:

- R9, R10 and R11 individually represent a saturated or unsaturated, hydroxylated or non-hydroxylated hydrocarbon radical having from 5 to 13 carbon atoms.

The trehalolipids can be produced by bacterial fermentation using the marine bacterium *Arthrobacter* sp. Ek 1 or the freshwater bacterium *Rhodococcus erythropolis*. Appropriate fermentation methods are provided by Ishigami et al. (1987), J. Jpn. Oil Chem. Soc., 36, 847-851, Schultz et al. (1991), Z. Naturforsch., 46C, 197-203, and Passeri et al. (1991), Z. Naturforsch., 46C, 204-209.

Cellobiose Lipids

The one or more glycolipids may be cellobiose lipids, which contain a cellobiose fragment and can be represented by the general formula (V):

(V)

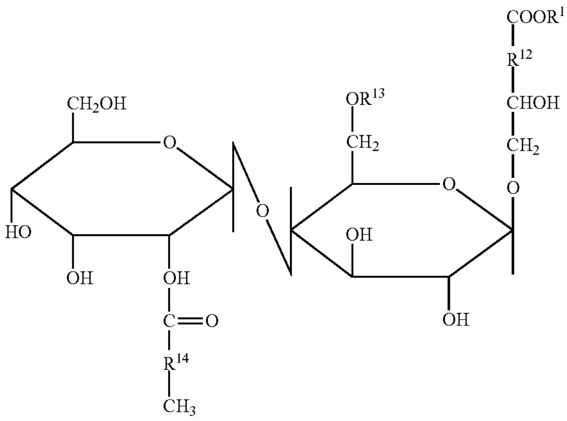

in which:

- R1 represents a hydrogen atom or a cation,
- R12 represents a saturated or unsaturated, hydroxylated or non-hydroxylated hydrocarbon radical having from 9 to 15 carbon atoms, preferably 13 carbon atoms,
- R13 represents a hydrogen atom or a acetyl group;
- R14 represents a saturated or unsaturated, hydroxylated or non-hydroxylated hydrocarbon radical having from 4 to 16 carbon atoms.

The cellobiose lipids can be produced by cells of fungi of the genus *Ustilago*. Appropriate fermentation processes are provided by Frautz, Lang and Wagner (1986), Biotech. Letts., 8, 757-762.

Rhamnolipids:

The one or more glycolipids may be rhamnolipids.

The composition according to the invention preferably comprises one or more rhamnolipids.

Rhamnolipids are glycolipids produced by various bacterial species. They consist of one rhamnose fragment (mono-rhamnolipid) or of two rhamnose fragments (di-rhamnolipid) linked by a glycosidic bond to one, two or three chains of β-hydroxylated fatty acids linked to one another by an ester bond.

More specifically, these mono-rhamnolipids and di-rhamnolipids correspond to the following formula (VI):

(VI)

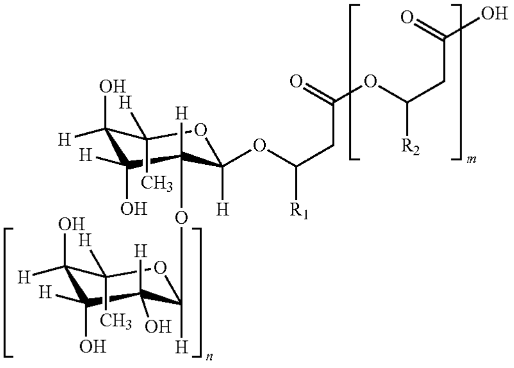

in which:

- m denotes an integer equal to 2, 1 or 0,
- n denotes an integer equal to 1 or 0, and
- R1 and R2, each independently represent identical or different hydrocarbon radicals having from 2 to 24 carbon atoms, preferably from 5 to 13 carbon atoms, that are branched or unbranched, substituted or unsubstituted, in particular hydroxy-substituted, and saturated or unsaturated, preferably a singly, doubly or triply unsaturated alkyl radical.

Thus, when n is equal to 0, the formula (VI) protects mono-rhamnolipids and, when n is equal to 1, it protects di-rhamnolipids.

The composition according to the invention preferably comprises at least one di-rhamnolipid.

The composition according to the invention preferably comprises at least one di-rhamnolipid of formula (VI) in which:

- m denotes an integer equal to 2, 1 or 0;
- n denotes an integer equal to 1; and
- R1 and R2, each independently represent identical or different hydrocarbon radicals having from 2 to 24 carbon atoms, preferably from 5 to 13 carbon atoms, that are branched or unbranched, substituted or unsubstituted, in particular hydroxy-substituted, and saturated or unsaturated, preferably a singly, doubly or triply unsaturated alkyl radical, and also the salts thereof, solvates thereof and optical isomers thereof.

The glycosidic bond between the two rhamnose fragments may be in the alpha or beta configuration and is preferably in the alpha configuration.

In the context of the invention,

- the salts of the di-rhamnolipids of formula (VI) are more particularly the carboxylate salts thereof with an organic or inorganic cation and especially with a cation selected from sodium, potassium, calcium and ammonium.
- the solvated forms of the di-rhamnolipids of formula (VI) are more particularly those solvated with one or more molecules of water or of organic solvents, for example a hydrate or a solvate of a linear or branched alcohol, such as ethanol or isopropanol, the optically active carbon atoms of the fatty acids preferably being in the form of the R enantiomers, and
- the term "alkyl" radical denotes a saturated, linear or branched aliphatic group; for example, a C1-C20 alkyl group having a linear or branched hydrocarbon chain of 1 to 20 carbon atoms, more particularly a methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or eicosyl.

The composition according to the invention preferably comprises at least one di-rhamnolipid of formula (VI) in which:

m denotes an integer equal to 2, 1 or 0;

n denotes an integer equal to 1; and

R1 and R2, which are identical or different, are selected from pentenyl, hexenyl, heptenyl, octenyl, nonenyl, decenyl, undecenyl, dodecenyl and tridecenyl radicals and radicals of formula —(CH2)oCH3, with o denoting an integer ranging from 1 to 23, in particular from 3 to 15 and more particularly from 4 to 12.

According to one embodiment of the invention, the composition according to the invention comprises at least one di-rhamnolipids of general formula (VI) in which m is equal to 1

According to one embodiment of the invention, the composition according to the invention comprises a mixture of at least two, preferably at least three, di-rhamnolipids of general formula (VI) in which m is preferably equal to 1.

According to another embodiment of the invention, the composition according to the invention comprises a mixture comprising at least one mono-rhamnolipid.

More preferably, the composition according to the invention comprises at least one dirhamnolipid of the following formula (VII):

(VII)

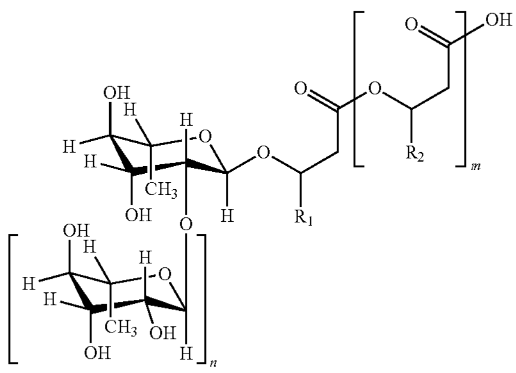

in which:

m denotes an integer equal to 2, 1 or 0; preferably, m is equal to 1, n denotes an integer equal to 1, R1 is a —(CH2)p-CH3 radical, with p being an integer varying from 1 to 23, preferably from 4 to 12, R2 is a —(CH2)q-CH3 radical, with q being an integer varying from 1 to 23, preferably from 4 to 12, and also the salts thereof, solvates thereof and optical isomers thereof.

By way of illustration and without limiting the di-rhamnolipids of formula (VII) that may be suitable for the invention, mention may be made in particular of the compounds of formula di-RL-CXCY, such as are defined in Table 1 below.

The formula di-RL-CXCY is an alternative way of writing in order to represent a di-rhamnolipid (di-RL) functionalized by two radicals R1 and R2 respectively represented by the symbols CX and CY, the integers X and Y being respectively equal to p+4 and q+4.

TABLE 1

| di-rhamnolipids of Formula (VII) | | | |
|---|---|---|---|
| Composés | Di-RL-CXCY | p | q |
| 1 | diRL-C8C8 | 4 | 4 |
| 2 | diRL-C8C10 | 4 | 6 |
| 3 | diRL-C10C8 | 6 | 4 |
| 4 | diRL-C10C10 | 6 | 6 |
| 5 | diRL-C10C12 | 6 | 8 |
| 6 | diRL-C12C10 | 8 | 6 |
| 7 | diRL-C12C12 | 8 | 8 |
| 8 | diRL-C12C14 | 8 | 10 |
| 9 | diRL-C14C12 | 10 | 8 |
| 10 | diRL-C14C14 | 10 | 10 |
| 11 | diRL-C14C16 | 10 | 12 |
| 12 | diRL-C16C14 | 12 | 10 |
| 13 | diRL-C16C16 | 12 | 12 |

According to a preferred embodiment, the composition according to the invention comprises at least one di-rhamnolipid of formula (VII) in which p and q are identical and equal to 6 and m is equal to 1, also referred to as di-RL-C10C10, or one of the salts, solvates and optical isomers thereof.

Preferably, the di-rhamnolipid of formula (VII) in which p and q are identical and equal to 6 and m is equal to 1 is present in the composition according to the invention in a proportion of at least 50% by weight and preferably of from 51% to 85% by weight, relative to the total weight of rhamnolipids.

According to another embodiment, the composition according to the invention comprises at least one di-rhamnolipid of formula (VII) in which m is equal to 1, p is equal to 6 and q is equal to 8.

According to another embodiment, the composition according to the invention comprises at least one di-rhamnolipid of formula (VI) in which n and m are equal to 1, R1 represents a —(CH2)oCH3 radical, with o being an integer varying from 4 to 12, and R2 is selected from the pentenyl, hexenyl, heptenyl, octenyl, nonenyl, decenyl, undecenyl, dodecenyl and tridecenyl radicals; preferably, R1 represents a —(CH2)6CH3 radical and R2 a nonenyl radical.

According to another preferred embodiment, the composition according to the invention comprises a mixture of at least two, in particular at least three, di-rhamnolipids of formula (VI) or of formula (VII) selected from:

a di-rhamnolipid of formula (VII) in which p and q are identical and equal to 6 and m is equal to 1;

a di-rhamnolipid of formula (VII) in which m is equal to 1, p is equal to 6 and q is equal to 8; and at least one di-rhamnolipid of formula (VI) in which n and m are equal to 1, R1 represents a —(CH2)oCH3 radical, with o being an integer varying from 4 to 12, and R2 is selected from the pentenyl, hexenyl, heptenyl, octenyl, nonenyl, decenyl, undecenyl, dodecenyl and tridecenyl radicals; preferably, R1 represents a —(CH2)6CH3 radical and R2 a nonenyl radical.

Preferably, the composition according to the invention comprises a mixture of at least two, in particular at least three, di-rhamnolipids of formula (VI) or of formula (VII) selected from:

at least 50% by weight and preferably of from 51% to 85% by weight of a di-rhamnolipid of formula (VII) in which p and q are identical and equal to 6 and m is equal to 1, relative to the total weight of rhamnolipids.

from 0.5% to 25% by weight, preferably from 5% to 15% by weight, of a dirhamnolipid of formula (VII) in which p is equal to 6, q is equal to 8 and m is equal to 1, relative to the total weight of rhamnolipids, and from 0.5% to 15% by weight, preferably from 3% to 12% by weight, preferably from 5% to 10% by weight, of a dirhamnolipid of formula (VI) in which n and m are equal to 1, R1 represents a —(CH2)6CH3 radical and R2 represents a nonenyl radical, relative to the total weight of rhamnolipids.

As specified above, rhamnolipids are customarily prepared by processes known to those skilled in the art starting from bacterial producers, such as *Pseudomonas.*

Appropriate fermentation methods are reviewed by D. Haferburg, R. Hommel, R. Claus and H. P. Kleber in Adv. Biochem. Ing./Biotechnol. (1986), 33, 53-90, and by F. Wagner, H. Bock and A. Kretschmar in Fermentation (ed. R. M. Lafferty) (1981), 181-192, Springer Verlag, Vienna.

Use may be made, as rhamnolipid, of the one sold under the name Rheance One by Evonik (INCI name: glycolipids).

In preferred embodiments, the at least one glycolipid is chosen from rhamnolipids, sophorolipids, or mixtures thereof.

The total concentration of the at least one amphoteric surfactant and the at least one glycolipid is about 10% to about 20% of the total weight of the composition. The ratio of the at least one amphoteric surfactant to the at least one glycolipid is from about 0.4 to about 4. The at least one glycolipid may be present in the cosmetic cleansing composition, for example, in a range from about 3% to about 7%, based on the weight of the cosmetic cleansing composition.

For example, the at least one glycolipid may be present in the cosmetic cleansing composition according to the disclosure from about from about 3% to about 7%, or from about 3% to about 6%, or from about 3% to about 5%, or from about 3% to about 4%, or from about 3% to about 7%, or from about 4% to about 7%, or from about 5% to about 7%, or from about 6% to about 7%, or any suitable combination, sub-combination, range, or sub-range thereof by weight, based on the weight of the cosmetic cleansing composition. One of ordinary skill in the art, however, will appreciate that other ranges are within the scope of the invention.

Cationic Polymer:

In the various embodiments, the cosmetic cleansing composition comprises at least one cationic polymer selected from nature-based polymers that are polysaccharides, and other natural (i.e., plant, animal, or bacterial based), synthetic, or modified cationic nature-based or synthetic polymers.

In some embodiments, the cationic polymer is a nature-based polymer. In general, a cationic nature-based polymer may be selected from cationic forms and cationic derivatives of polysaccharides isolated from algae, polysaccharides produced by microorganisms, and polysaccharides from higher plants, such as homogeneous polysaccharides.

In some embodiments, cationic nature-based polymer selected from polysaccharides may be chosen from polysaccharides that include chitosan, chitin, starches, alginates, celluloses, galactomannans such as guar gums, particularly cationic derivatives thereof, and combinations thereof. In some embodiments, the at least one cationic nature-based polymer selected from polysaccharides may be chosen from chitosan, chitosan derivatives, chitin, starch, starch derivatives, cellulose (for example, but not limited to, ethylcellulose, nitrocellulose, hemicellulose, and hemicellulose derivatives), alginates, including but not limited to, sodium alginate, and combinations thereof.

In some embodiments, the cationic polymer is a nature-based cationic polymer selected from: chitosan, chitosan oligosaccharide, polymeric chitosan having MW in a range from 1 kDa to about 1000 kDa, derivatives of chitosan, derivatives of chitosan having enhanced solubility, cyclodextrin, cationic gelatin, cationic dextran, cationic cellulose, polylysine, polyornithine, histone, collagen, chitosan-cysteine, chitosan-thiobutylamidine, chitosan-thioglycolic acid, or combinations thereof. In preferred embodiments, the cationic polymer is selected from chitosan, polylysine, or combinations thereof.

Examples of cationic polymers include polysaccharide-based delivery molecules (e.g., chitosan, cyclodextrin, cationic gelatin, cationic dextran, cationic cellulose), cationic peptides and their derivatives (e.g., polylysine, polyornithine), peptide/protein polymers ((e.g., histone, collagen), linear or branched synthetic polymers (e.g., polybrene, polyethyleneimine), natural polymers (e.g., histone, collagen), synthetic dendrimers, cationic thiolated biopolymers (nature-based thiomers or nature-based dendrimers, e.g., chitosan-cysteine, chitosan-thiobutylamidine as well as chitosan-thioglycolic acid).

Examples of nature-based cationic polymers include polysaccharide-based delivery molecules (e.g., chitosan, cyclodextrin, cationic gelatin, cationic dextran, cationic cellulose); cationic peptides and their derivatives (e.g., polylysine, polyornithine), peptide/protein polymers (e.g., histone, collagen); cationic thiolated biopolymers (nature-based thiomers or nature-based dendrimers, e.g., chitosan-cysteine, chitosan-thiobutylamidine, chitosan-thioglycolic acid); or combinations thereof.

In some embodiments, the cosmetic cleansing composition comprises the at least one nature-based cationic chitosan selected from chitosan oligosaccharide, chitosan (or polymeric chitosan having molecular weight (MW) in a range from about 1 kDa to about 1000 kDa), derivatives of chitosan, including derivatives having enhanced solubility, or combinations thereof.

In various embodiments, chitosan has a molecular weight (MW) in a range from about 1 kDa to about 1000 kDa. In some particular embodiments, chitosan has a MW that is "low" and is in the range from about 1 kDa to about 20 kDa, or from about 10 kDa to about 20 kDa, or from about 12 kDa to about 18 kDa. In some embodiments, the chitosan has a Chitosan MW=~27 kDa According to the present invention, the cationic polymer may be selected from polylysines. A single type of polylysines may be used, or two or more different types of polylysines may be used in combination.

Polylysines correspond to the condensation of several amino acids of lysine. Polylysine can be a natural homopolymer of L-lysine that can be produced by bacterial fermentation. Polylysines are typically used as a natural preservative in food products. Polylysine is a polyelectrolyte which is soluble in polar solvents such as water.

Polylysine can be, for example, epsilon-polylysine (or referred as "ε-polylysine"), which is a condensation of amino groups at the ε-position and carboxyl groups of lysines, or alpha-polylysine (or referred as "α-polylysine"), which is a condensation of amino groups at the α-position and carboxyl groups of lysines. Polylysine is commercially available in various forms, such as poly D-lysine and poly L-lysine. The polylysine is generally a condensate of L-lysines, i.e., poly L-lysine.

As an example of polylysine, mention may be made of:

Epsilon-poly-L-lysine of JNC CORPORATION which is a 25% solution of Epsilon-poly-L-lysine having a molecular weight of around 4,700 in aqueous solution.

The polylysine may be in the form of organic or inorganic salts. The addition salts with an acid are, for example, the hydrochloric or hydrobromic acid, sulfuric acid, citric acid, succinic acid, tartaric acid, lactic acid, para-toluenesulphonic acid, phosphoric acid, or acetic acid salts; or fatty acid salts, such as linoleic acid, oleic acid, palmitic acid, stearic acid, behenic acid, and 18-methylicosanoic acid. The addition salts with a base are, for example, a sodium salt, a calcium salt, or a hydroxyalkylamine salt, for example, N-methylglucamine, aminopropane diol or triethanolamine.

In some preferred embodiments of the present invention, the polylysine of the present invention is present in a form of a single molecule in the composition, or is not covalently bound to other compounds. In one embodiment of the present invention, the polylysine is not covalently bound to dye compounds. In one embodiment of the present invention, the polylysine is not covalently bound to polyorganosiloxane compounds. The term "polyorganosiloxane" is well-known in the art to mean compounds having Si—O main chain and organic functional groups attached to the main chain.

In another embodiment of the present invention, the polylysine is in the free form. The term "free form" here indicates that the polylysine is not covalently bound to any other compounds.

The at least one nature-based cationic polymer is present in the cosmetic cleansing composition according to the disclosure from about 0.05% to about 2%, or from about 0.05% to about 1%, or from about 0.05% to about 1%, or from about 0.1% to about 0.5%, or from about 0.1% to about 0.2%, or any suitable combination, sub-combination, range, or sub-range thereof by weight, based on the weight of the cosmetic cleansing composition. One of ordinary skill in the art, however, will appreciate that other ranges are within the scope of the invention.

Thus, one or a combination of polymers may be present, by weight, based on the total weight of the cosmetic cleansing composition, from about 0.05, 0.06, 0.07, 0.08, 0.90, 0.1, 0.2, 0.3, 0.4, 0.5, 0.6, 0.7, 0.8, 0.9, 1.0, to about 2 weight percent, including increments and ranges therein and there between.

In other embodiments, cationic nature-based polymer selected from polysaccharides may be chosen from one or more of methylcelluloses, hydroxyalkylcelluloses, ethylhydroxyethylcelluloses and carboxymethylcelluloses, mannans, xylans, lignins, arabans, galacturonans, alginate-based compounds, chitin, glucuronoxylans, arabinoxylans, xyloglucans, glucomannans, fructosans such as inulin, pectic acids and pectins, arabinogalactans, agars, glycosaminoglycans, gum arabics, tragacanth gums, ghatti gums, karaya gums, locust bean gums, biopolysaccharide gums of microbial origin such as scleroglucan or xanthan gums, mucopolysaccharides, chondroitin sulfates, and mixtures thereof.

In some embodiments, the cationic polymer is not a nature-based polymer and may be selected from synthetic polymers. In some examples, the synthetic polymers are non-silicone based, and in some embodiments may be selected from the group consisting of polyquaterniums, that is polymers having quaternary ammonium centers in the polymer, for example, including polyquaternium-47 (1-Propanaminium. N,N,N-trimethyl-3-[(2-methyl-1-oxo-2-propenyl)amino]-, chloride, polymer with methyl 2-propenoate and 2-propenoic acid). Other non-limiting examples of such polyquaternium compounds may be selected from diallyidimethylammonium chloride/acrylic acid copolymers sold under the names MERQUAT 280 POLYMER or MERQUAT 280NP POLYMER or MERQUAT 281 POLYMER or MERQUAT 295 POLYMER, by the company Nalco (Lubrizol) (INCI name: Polyquaternium-22); the copolymer of methacrylamidopropyltrimonium chloride, of acrylic acid and or methyl acrylate, sold under the name MERQUAT 2001 POLYMER OR MERQUAT 2001N POLYMER by the company Nalco (Lubrizol) (INCI name: Polyquaternium-47); the acrylamide/dimethyldiallylammonium chloride/acrylic acid terpolymer sold under the name MERQUAT 3330DRY POLYMER or MERQUAT 3330PR POLYMER or MERQUAT 3331PR POLYMER or MERQUAT 3940 POLYMER or MERQUAT PLUS 3330 POLYMER OR MERQUAT PLUS 3331 POLYMER by the company Nalco (Lubrizol) (INCI name: Polyquaternium-39); an ampholytic terpolymer consisting of methacrylamidopropyl trimethyl ammonium chloride (MAPTAC), acrylamide and acrylic acid, sold under the name MERQUAT 2003PR POLYMER by the company Nalco (Lubrizol) (INCI name: Polyquaternium-53); Polyquaternium-30, Polyquaternium-35, Polyquaternium-45, Polyquaternium-50, Polyquaternium-54; Polyquaternium-57; Polyquaternium-63; Polyquaternium-74; Polyquaternium-76; Polyquaternium-86; Polyquaternium-89; Polyquaternium-95; Polyquaternium-98, Polyquaternium-104; Polyquaternium-111; Polyquaternium-112, and mixtures thereof. In some embodiments, the cationic polymer is a synthetic polymer selected from cationic acrylic polymers, for example, an amorphous functional acrylic polymer grafted onto a polyethylene backbone such as SYNTRAN™ 5330, which is a quaternary modified olefin grafted technology. More generally, such synthetic polymers selected from, but are not limited to, cationic polymers comprising polyacrylates such as those identified in the International Cosmetic Ingredient Dictionary and Handbook (9 th ed. 2002) such as, for example, polyacrylate-1, polyacrylate-2, polyacrylate-3, polyacrylate-4, polyacrylate-16, polyacrylate-17, polyacrylate-18, polyacrylate-19, polyacrylate-21, and mixtures thereof. Such (co) polymers, or similar (co) polymers, can be combined individually or with other (co) polymers in such a way to form suitable bimodal agents having both cationic and anionic functionalities.

In the various embodiments, the amount of cationic polymer is not a nature-based polymer and is selected from synthetic cationic polymers that may be present in the cosmetic cleansing composition can range from about 0.05% to about 2%, or from about 0.05% to about 1%, or from about 0.05% to about 1%, or from about 0.1% to about 0.5%, or from about 0.1% to about 0.2%, or any suitable combination, sub-combination, range, or sub-range thereof by weight, based on the weight of the cosmetic cleansing composition.

Thus, any one of the at least synthetic cationic polymer, when present, is present, by weight, based on the total weight of the cosmetic cleansing composition, from about 0.05, 0.06, 0.07, 0.08, 0.09, 0.1, 0.2, 0.3, 0.4, 0.5, 0.6, 0.7, 0.8, 0.9, 1, to about 2 weight percent, including increments and ranges therein and there between.

In the various embodiments, the amount of each of the at least one cationic polymer which may be either nature-based or synthetic cationic polymer, alone or in combination with another cationic polymer, present in the cosmetic cleansing compositions can range from about 0.05% to about 2%, or from about 0.05% to about 1%, or from about 0.05% to about 1%, or from about 0.1% to about 0.5%, or from about 0.1% to about 0.2% or any suitable combination, sub-combination, range, or sub-range thereof by weight, based on the weight of the cosmetic cleansing composition. One of ordinary skill in the art, however, will appreciate that other ranges are within the scope of the invention.

In preferred embodiments, according to the invention the cationic polymer is chosen from nature based cationic polymers.

Compositions according to the disclosure contain at least one cosmetically acceptable solvent. In various embodiments, the cosmetically acceptable solvent may be chosen from water.

Cosmetic cleansing compositions according to the disclosure are essentially free of phenoxyethanol.

In various embodiments, the compositions have a pH from about 4 to about 8. For example, the pH of the compositions may range from about 4.5 to about 7.5, including all ranges and subranges therebetween.

DEFINITIONS AND TERMS

As used herein, the phrases "and mixtures thereof," "and a mixture thereof," "and combinations thereof," "and a combination thereof," "or mixtures thereof," "or a mixture thereof," "or combinations thereof," and "or a combination thereof," are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

The transitional terms "comprising", "consisting essentially of" and "consisting of", when used in the appended claims, in original and amended form, define the claim scope with respect to what unrecited additional claim elements or steps, if any, are excluded from the scope of the claim(s). As used herein, the terms "comprising," "having," and "including" (or "comprise," "have," and "include") are used in their open, non-limiting sense. The term "comprising" is intended to be inclusive or open-ended and does not exclude any additional, unrecited element, method, step, or material. The term "consisting of" excludes any element, step, or material other than those specified in the claim and, in the latter instance, impurities ordinary associated with the specified material(s). The term "consisting essentially of" limits the scope of a claim to the specified elements, steps, or material (s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

In this application, the use of the singular includes the plural unless specifically stated otherwise. The singular forms "a," "an," "the," and "at least one" are understood to encompass the plural as well as the singular unless the context clearly dictates otherwise, and these expressions, as well as the expression "one or more" which means "at least one," are expressly intended to include the individual components as well as mixtures/combinations thereof.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. All ranges and amounts given herein are intended to include sub-ranges and amounts using any disclosed point as an end point. All numbers, amounts, ranges, etc., are intended to be modified by the term "about," whether or not so expressly stated. Similarly, a range given of "about 3% to 7%" is intended to have the term "about" modifying both the 3% and the 7% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

"Active material" as used herein with respect to the percent amount of an ingredient or raw material, refers to 100% activity of the ingredient or raw material.

All amounts given herein are relative to the amount of active material, unless otherwise indicated.

All percentages, parts and ratios herein are based upon the total weight of the compositions of the present disclosure, unless otherwise indicated.

As used herein, the term "surfactants," as well as any specifically-identified surfactants, includes salts of the surfactants even if not explicitly stated.

As used herein, the term "synthetic" means a material that is not of natural origin. The term "natural" and "naturally-sourced" and "nature-based" means a material of natural origin, such as derived from plants, which also cannot be subsequently chemically or physically modified. "Plant-based" means that the material came from a plant.

Unless otherwise expressly stated, it is in no way intended that any method set forth herein be construed as requiring that its steps be performed in a specific order. Accordingly, where a method claim does not expressly recite an order to be followed by its steps or it is not specifically stated in the claims or descriptions that the steps are to be limited to a specific order, it is no way intended that any particular order be inferred.

As used herein, the term "substantially free" or "essentially free" as used herein means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in a raw material that is included in the composition.

EXAMPLES

The following examples are intended to be non-limiting and explanatory in nature only. In the Examples, amounts are expressed in percentage by weight (wt %) of active materials, relative to the total weight of the composition.

Example 1—Coacervate Examples

In order to demonstrate the coacervate phenomenon according to the disclosure, the following compositions (A-D) were prepared.

TABLE 2

| Inventive Compositions | | | | |
|---|---|---|---|---|
| | Inventive Compositions | | | |
| INCI Name | A | B | C | D |
| Cocamidopropyl hydroxysultaine | 5% | 5% | 5% | |
| Coco Betaine | | | | 5% |
| Rhamnolipid | | | 4% | 4% |
| Sophorolipid | 4% | 4% | | |
| Chitosan | | 0.1% | | 0.1% |
| Polylysine | 0.2% | | 0.1% | |
| Water | 90.8% | 90.9% | 90.9% | 90.9% |
| pH | 6.2 | 5.2 | 5.2 | 4.85 |
| Phase behavior after 10x dilution | hazy | hazy | hazy | hazy |

Figure 2:
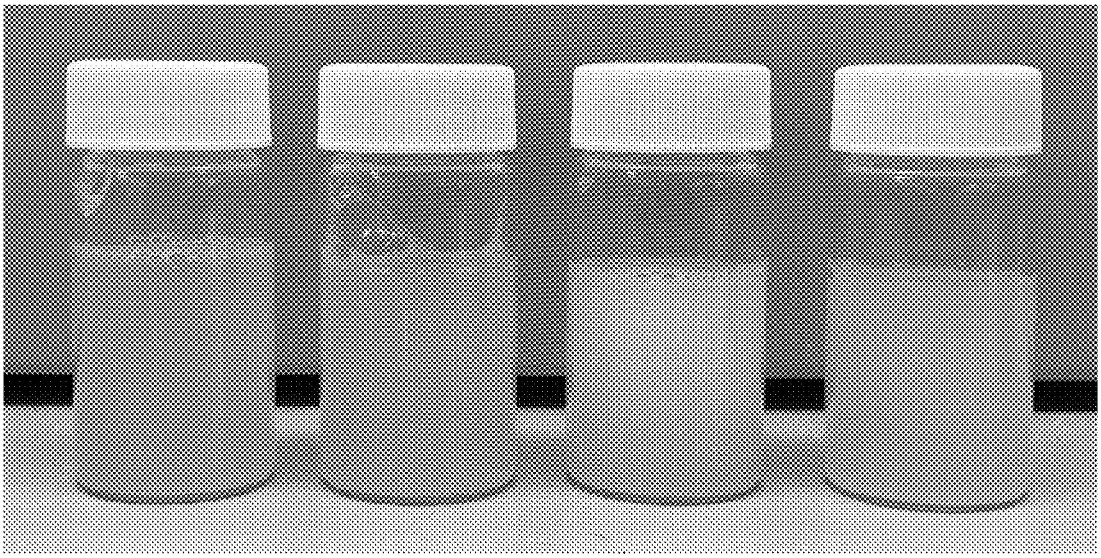
FIG. 2. Coacervate cleansing system compositions A-D after dilution with water.

Each of compositions (A-D) were clear upon initial preparation as shown in FIG. 1. After dilution 10 times with water, the compositions appeared hazy, as shown in FIG. 2. Each of compositions A-D demonstrated the coacervate phenomenon by going through the phase transition during dilution with water. The coacervate cleansing system in examples A-D demonstrated enhanced removability of makeup and good stability.

Example 2—Coacervate System with Sophorolipid

In order to demonstrate the coacervate phenomenon according to the disclosure, the following inventive compositions (3-7) and comparative compositions (1, 2, 8, and 9) were prepared.

TABLE 3

| Compositions with Cocamidopropyl Hydroxysultaine, Sophorolipid and Chitosan - Behavior After Dilution | | | | | | |
|---|---|---|---|---|---|---|
| Sample | A % | B % | Chitosan % | Water | pH | Phase Behavior after dilution 2-10× |
| 1 | 1% | 9% | 0.1% | 89.9% | 4.5-6.5 | Solution not clear |
| 2 | 2% | 8% | 0.1% | 89.9% | 4.5-6.5 | Solution not clear |
| 3 | 3% | 7% | 0.1% | 89.9% | 4.5-6.5 | Cloudy/precipitates when diluted |
| 4 | 4% | 6% | 0.1% | 89.9% | 4.5-6.5 | Cloudy/precipitates when diluted |
| 5 | 5% | 5% | 0.1% | 89.9% | 4.5-6.5 | Cloudy/precipitates when diluted |
| 6 | 6% | 4% | 0.1% | 89.9% | 4.5-6.5 | Cloudy/precipitates when diluted |
| 7 | 7% | 3% | 0.1% | 89.9% | 4.5-6.5 | Cloudy/precipitates when diluted |
| 8 | 8% | 2% | 0.1% | 89.9% | 4.5-6.5 | No coacervate |
| 9 | 9% | 1% | 0.1% | 89.9% | 4.5-6.5 | No coacervate |

A = Cocamidopropyl Hydroxysultaine; B = Sophorolipid

Compositions 1-9 were prepared, and then diluted 10 times with water. Samples 3-7 demonstrated the coacervate phenomenon and turned cloudy after dilution with water. Samples 1, 2, 8, and 9 did not demonstrate coacervate, and did not turn cloudy after dilution. Samples with sophorolipid concentrations between 3 and 7%, and cocamidopropyl hydroxysultaine concentrations between 3 and 7% demonstrated coacervate.

The coacervate cleansing system in examples 3-7 demonstrated enhanced removability of makeup and good stability.

Example 3—Coacervate System with Rhamnolipid

In order to demonstrate the coacervate phenomenon according to the disclosure could be achieved across a range of concentrations, the following compositions containing varying amounts of cocamidopropyl hydroxysultaine, rhamnolipid, and polylysine were prepared.

TABLE 4

| Compositions with Cocamidopropyl Hydroxysultaine, Rhamnolipid and Polylysine - Behavior After Dilution | | | | | | |
|---|---|---|---|---|---|---|
| Sample | A % | C % | Polylysine % | Water | pH | Phase Behavior |
| 10 | 1% | 9% | 0.1% | 89.9% | 4.5-7.5 | No coacervate |
| 11 | 2% | 8% | 0.1% | 89.9% | 4.5-7.5 | No coacervate |
| 12 | 3% | 7% | 0.1% | 89.9% | 4.5-7.5 | Cloudy/precipitates when diluted |
| 13 | 4% | 6% | 0.1% | 89.9% | 4.5-7.5 | Cloudy/precipitates when diluted |
| 14 | 5% | 5% | 0.1% | 89.9% | 4.5-7.5 | Cloudy/precipitates when diluted |
| 15 | 6% | 4% | 0.1% | 89.9% | 4.5-7.5 | Cloudy/precipitates when diluted |
| 16 | 7% | 3% | 0.1% | 89.9% | 4.5-7.5 | Cloudy/precipitates when diluted |
| 17 | 8% | 2% | 0.1% | 89.9% | 4.5-7.5 | Cloudy/precipitates when diluted |
| 18 | 9% | 1% | 0.1% | 89.9% | 4.5-7.5 | No Coacervate |

A = Cocamidopropyl Hydroxysultaine; C = Rhamnolipid

Compositions 10-18 were prepared, and then diluted 10 times with water. Samples 12-17 demonstrated the coacervate phenomenon and turned cloudy after dilution with water. Samples 10, 11, and 18 did not demonstrate coacervate, and did not turn cloudy after dilution. Samples with rhamnolipid concentrations between 2 and 7%, and cocamidopropyl hydroxysultaine concentrations between 3 and 8% demonstrated coacervate.

The coacervate cleansing system in examples 12-17 demonstrated enhanced removability of makeup and good stability.

The invention claimed is:

1. A coacervate cleansing system, comprising a composition comprising:

(a) at least one amphoteric surfactant including cocamidopropyl hydroxysultaine;

(b) at least one glycolipid;

(c) at least one cationic polymer from about 0.05% to about 0.2%, by weight, and chosen from chitosan, polylysine, or a mixture thereof, and (d) at least one cosmetically acceptable solvent;

wherein the cleansing system is essentially free of phenoxyethanol, wherein the pH of the composition is between 4 and 8, wherein the weight ratio of the at least one amphoteric surfactant to the at least one glycolipid is from about 0.4 to about 4, and wherein the total concentration of the at least one amphoteric surfactant and the at least one glycolipid combined is about 9 to about 20% of the total weight of the composition.

2. The system of claim 1, wherein the at least one amphoteric surfactant further includes at least one of cocamidopropyl betaine, coco betaine, sodium lauroamphoacetate, disodium cocoamphodiacetate or a mixture thereof.

3. The system of claim 1, wherein the at least one glycolipid is chosen from rhamnolipids, sophorolipids, glucolipids, trehalolipids, cellobiose lipids, mannosylerythritol lipid, or a mixture thereof.

4. The system of claim 1, the composition further comprising at least one additional cosmetic ingredient.

5. The system of claim 2, wherein the amphoteric surfactant includes a combination of the cocamidopropyl hydroxysultaine and the coco-betaine.

6. The system of claim 3, wherein the at least one glycolipid is chosen from sophorolipids, rhamnolipids, or a mixture thereof.

7. The system of claim 2, wherein the concentration of amphoteric surfactant is from about 3% to about 8%.

8. The system of claim 3, wherein the concentration of glycolipid is from about 2% to about 7%.

9. The system of claim 1, wherein the concentration of cationic polymer is from about 0.1 to about 0.2%.

10. The system of claim 1, wherein the pH is from 4.5-7.5.

11. A coacervate cleansing system comprising a composition comprising:

(a) at least one amphoteric surfactant selected from the group consisting of cocamidopropyl hydroxysultaine and coco betaine from about 3% to about 8% by weight, relative to the total weight of the composition;

(b) at least one glycolipid selected from the group consisting of rhamnolipid and sophorolipid from about 2% to about 7% by weight, relative to the total weight of the composition;

(c) at least one cationic polymer selected from the group consisting of chitosan and polylysine from about 0.1% to about 0.2%; and (d) water; wherein:

i) the composition is an aqueous composition;

ii) the composition is free of polyquaternium cationic polymers;

iii) the cleansing system is essentially free of phenoxyethanol;

iv) the pH of the composition is between 4 and 8;

v) the weight ratio of the at least one amphoteric surfactant to the at least one glycolipid is from about 0.4 to about 4; and vi) the total concentration of the at least one amphoteric surfactant and the at least one glycolipid combined is about 9% to about 20% of the total weight of the composition.

12. A method for cleansing skin comprising applying to the skin of a subject a coacervate cleansing system comprising a composition comprising:

(a) at least one amphoteric surfactant selected from the group consisting of cocamidopropyl hydroxysultaine and coco betaine from about 3% to about 8% by weight, relative to the total weight of the composition;

(b) at least one glycolipid selected from the group consisting of rhamnolipid and sophorolipid from about 2% to about 7% by weight, relative to the total weight of the composition;

(c) at least one cationic polymer selected from the group consisting of chitosan and polylysine from about 0.1% to about 0.2%; and (d) at least one cosmetically acceptable solvent, including water; wherein:

i) the composition is an aqueous composition;

ii) the composition is free of polyquaternium cationic polymers;

iii) the cleansing system is essentially free of phenoxyethanol;

iv) the pH of the composition is between 4 and 8;

v) the weight ratio of the at least one amphoteric surfactant to the at least one glycolipid is from about 0.4 to about 4; and vi) the total concentration of the at least one amphoteric surfactant and the at least one glycolipid combined is about 9% to about 20% of the total weight of the composition.

13. The method of claim 12, wherein the composition is rinsed off the skin.

14. The system of claim 1, wherein the weight ratio of the at least one amphoteric surfactant to the at least one glycolipid is from about 0.4 to 3.

15. The system of claim 11, wherein the weight ratio of the at least one amphoteric surfactant to the at least one glycolipid is from about 0.4 to 3.

16. The method of claim 12, wherein the weight ratio of the at least one amphoteric surfactant to the at least one glycolipid is from about 0.4 to 3.

* * * * *